United States Patent [19]
Ohmori et al.

[11] Patent Number: 5,466,673
[45] Date of Patent: Nov. 14, 1995

[54] METHOD OF INHIBITING CALCIUM PRECIPITATION IN AN INTRAOCULAR IRRIGATING SOLUTION

[75] Inventors: Shinji Ohmori, Okayama; Kazumi Ogata, Toyonaka; Hideki Tsuruoka, Kawanishi; Takahiro Sakaue, Itami, all of Japan

[73] Assignee: Senju Pharmaceutical Co., Ltd., Osaka, Japan

[21] Appl. No.: 253,304

[22] Filed: Jun. 3, 1994

[30] Foreign Application Priority Data

Jun. 7, 1993 [JP] Japan ................... 5-135909

[51] Int. Cl.⁶ .................... A61K 38/04; C07K 5/037
[52] U.S. Cl. .................... 514/18; 514/915
[58] Field of Search .................... 514/18, 915

[56] References Cited

U.S. PATENT DOCUMENTS 4,837,021   6/1989   Andermann et al. .......... 424/602

FOREIGN PATENT DOCUMENTS

0501354A1   9/1992   European Pat. Off. .

*Primary Examiner*—Jill Warden
*Assistant Examiner*—Benet Prickril
*Attorney, Agent, or Firm*—Wenderoth, Lind & Ponack

[57] ABSTRACT

This invention relates to an intraocular irrigating composition containing a compound of the following formula or a pharmacologically acceptable salt thereof

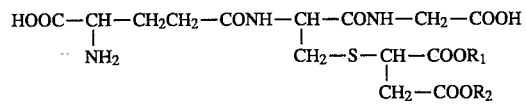

wherein $R_1$ and $R_2$ are the same or different and each represents a hydrogen atom or a methyl group.

The glutathione derivative contained in the intraocular irrigating solution of this invention is not only effective in protecting the intraocular tissues on the occasion of ophthalmic surgery but effectively inhibits precipitation of the calcium contained. Therefore, the intraocular irrigating solution of this invention is very stable and can be used with advantage in various kinds of ophthalmic surgery such as cataract surgery and transplantation of the cornea, iris and vitreous body.

11 Claims, No Drawings

METHOD OF INHIBITING CALCIUM PRECIPITATION IN AN INTRAOCULAR IRRIGATING SOLUTION

BACKGROUND OF THE INVENTION

1. Field of the Invention

This invention relates to a useful intraocular irrigating solution. More particularly, this invention relates to a useful intraocular irrigating solution characterized by containing S-(α,β-dicarboxyethyl)glutathione, which is a physiological substance, or an ester thereof, or a pharmacologically acceptable salt thereof.

2. Description of the Prior Art

With the recent progress and spread of cataract surgery and other ophthalmic surgery such as transplantation of the cornea, iris and vitreous body, there is a need for an intraocular irrigating solution effective enough to protect the intraocular tissues against damage during such operations. If the protection of intraocular tissues during operation is inadequate and the tissues sustain physiologic damage, the postoperative course will be unfavorable with an increased risk of complications such as corneal opacity, glaucoma and retinitis.

Any intraocular irrigating solution desirably approximates the human aqueous humor in composition but so far physiological saline, lactated Ringer's solution, BSS (balanced salt solution) PLUS (trade name), etc. have been chiefly utilized for intraocular irrigation and lavage.

However, these intraocular irrigating solutions are not sufficiently satisfactory for the protection of intraocular tissues and as far as BSS PLUS is concerned, it is not as stable as desired. Therefore, much research is underway for the development of a more stable, more tissue-protective intraocular irrigating solution.

Meanwhile, according to Kinseg et al., a desirable intraocular irrigating solution is composed of 8.33 mM glucose, 1.23 mM calcium, 1.22 mM magnesium and 25 mM sodium hydrogen carbonate and has a pH value of 7.4. However, this intraocular irrigating solution has the disadvantage that the calcium contained therein tends to precipitate with aging. As inhibitors of precipitation of calcium, several compounds can be contemplated but in order that such compounds may occur in amounts necessary to prevent precipitations as to inflict damages on the intraocular tissues. Thus, there is no agent as of today that is able to effectively prevent precipitation of calcium and yet keep the intraocular tissues intact and safe.

Under the circumstances the inventors of this invention, who had been studying the pharmacologic actions of S-(α,β-dicarboxyethyl)glutathione, which is a physiological substance occurring comparatively abundantly in the crystalline lens, in particular, or an ester thereof, or a pharmacologically acceptable salt thereof, discovered that any of these compounds not only exerts an excellent protective action on the intraocular tissues but also is useful for the inhibition of precipitation of calcium. This discovery was followed by further intensive research, which has culminated in the development of this invention.

SUMMARY OF THE INVENTION

This invention is, therefore, directed to (1) an intraocular irrigating solution characterized by containing a compound of the following formula

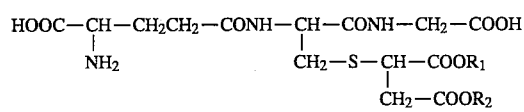

[wherein $R_1$ and $R_2$ are the same or different and each represents a hydrogen atom or a lower alkyl group] (hereinafter referred to briefly as the present compound) or a pharmacologically acceptable salt thereof and (2) an intraocular irrigating solution further containing calcium ions in addition to the compound or salt thereof.

DETAILED DESCRIPTION OF THE INVENTION

Among species of the present compound for use in the intraocular irrigating solution of this invention, S-(α,β-dicarboxyethyl) glutathione (abbreviated as DCE-GS) is a physiological substance which D. H. Calam and S. G. Waley discovered in the bovine lens (Biochem. J. 86, 226 (1963)) and the inventors of this invent ton already demonstrated the present compound has blood coagulation inhibitory activity (JP Kokoku 5-86931/1993), platelet aggregation inhibitory activity (JP Kokai 2-255624/1990), antiinflammatory/antiallergic activity (JP Kokai 3-48626/1991), antitumor activity (JP Kokai 3-112933/1991) and hepatic impairment inhibitory activity (JP Kokai 3-118334/1991).

Referring to the above chemical formula, the lower alkyl, designated by $R_1$ and $R_2$, is preferably an alkyl group of 1 to 10 carbon atoms. It may be a straight-chain, branched-chain or cyclic group and may even have a ring moiety. Thus, methyl, ethyl, n-propyl, i-propyl, n-butyl, t-butyl, sec-butyl, n-pentyl, 1-ethylpropyl, i-pentyl, etc. can be mentioned.

The present compound for use in the intraocular irrigating solution of this invention may be a free compound or a pharmacologically acceptable salt. The pharmacologically acceptable salt mentioned just above includes salts with alkali metals such as sodium, potassium, etc. and salts with alkaline earth metals such as calcium, magnesium, etc. and, for that matter, may be any other pharmacologically acceptable salt. These salts may be the salts involving all the carboxyl groups of the present compound or those involving less than all the carboxyl groups. The number of carboxyl groups forming such a salt is dependent on the type off salt and production pH but all of these salts can be selectively used in the manufacture of intraocular irrigating solution of this invention.

The present compound for use in the manufacture of the intraocular irrigating solution of this invention can be obtained by the known technology, for example as follows. Since S-(α,β-dicarboxyethyl ) glutathione occurs in yeasts, the bovine lens, etc., it can be isolated by the known extraction and purification procedures. Alternatively, S-(α,β-dicarboxyethyl)glutathione can be synthesized from glutathione by allowing an equimolar mixture of glutathione and maleic acid to stand in an aqueous or alcoholic aqueous medium under warming or at room temperature for 1 to 2 days. By using a mono- or diester of maleic acid in lieu of maleic acid, the corresponding ester of S-(α,β-dicarboxyethyl)glutathione can be similarly synthesized. All off these compounds contain asymmetric carbons and may, therefore, occur optical isomers but all of such isomers and any mixture thereof can be used for the purposes of the invention.

According to the intended use and need, the intraocular irrigating solution off this invention may contain one or more species of the present compound in suitable combination.

Since the present compound for use in the intraocular irrigating solution is a physiological substance or an ester thereof, it is of very low toxic potential and safe as will be clear from Reference Example 1 presented hereinafter, and can be used with advantage for the purposes of this invention.

The intraocular irrigating solution of this invention can be prepared by the method known in the Field of ophthalmic medicine.

The preferred concentration of the present compound in the intraocular irrigating solution of this invention is dependent on the species of compound but is generally about 0.1 mg/ml to about 10 mg/ml and preferably about 0.5 mg/ml to about 5 mg/ml.

Where calcium ions are to be included in the intraocular irrigating solution of this invention, the ions are added in the form of calcium salt of the present compound, calcium chloride, calcium acetate or the like. The preferred concentration of such a salt is generally about 0.5 mM to about 5 mM and preferably about 1 mM to about 1.5 mM.

The intraocular irrigating solution of this invention is preferably adjusted to pH about 6.5 to about 7.5 by the per se known procedure.

The osmotic pressure of the intraocular irrigating solution of this invention is preferably adjusted, by the per se known procedure, to about 260 mOsm to about 310 mOsm and preferably to about 275 mOsm to about 305 mOsm.

Unless contrary to the object of this invention, the intraocular irrigating solution of this invention may contain other ingredients which are commonly incorporated in intraocular irrigating solutions, e.g. various electrolytes such as magnesium chloride, magnesium sulfate, sodium chloride, potassium chloride, sodium acetate, sodium hydrogen carbonate, etc., and monosaccharides such as glucose in amounts commonly used.

The intraocular irrigating solution of this invention can be used appropriately in surgical operations other than ophthalmic surgery as well.

EXAMPLES

The following examples are further illustrative of this invention.

Example 1

Effect of the Present Compound on the Blood-Aqueous Barrier of the Eye

Experimental animals

White rabbits weighing about 2.5 kg were used.

Test solutions

Physiological saline, 0.06, 0.6 and 6 mM solutions of DCE-GS in physiological saline, and a 0.3 mM solution of GSSG (oxidized glutathione) in physiological saline were used as intraocular irrigating solutions and their effects on the blood-aqueous barrier of the eye were evaluated.

Method

Two 23 G needles connected to a polyethylene tube were gently inserted into the anterior chamber of the eye of rabbits under anesthesia (ketamine hydrochloride: xylazine hydrochloride=1:1) and 0.5 ml/kg of 1% carboxy-fluorescein was injected into the auricular vein immediately before irrigation. Using a syringe pump, the intraocular irrigating solution was infused at the rate of 1.5 ml/min. and 25 μl of the outflowing intraocular irrigating solution and the blood were respectively collected at 15-minute intervals over the period of 1 hour and the intensity of florescence of each sample was determined with a spectrophotofluorometer. The collected blood was mixed with 2.5 ml of physiological saline and the mixture was centrifuged at 3000 rpm to separate the supernatant for use as a sample.

The degree (4) of protein leakage was calculated by means of the following equation. (Intensity of fluorescence of irrigating solution/intensity of fluorescence of blood)× 100 (%)

Results

The results are shown in Table 1.

[TABLE 1]

| | Effect of the present compound on the blood-aqueous barrier of the eye | | | | |
|---|---|---|---|---|---|
| | | Time (min.) | | | |
| Group | n | 15 | 30 | 45 | 60 |
| Physiological saline | 11 | 0.24 ± 0.06 | 0.44 ± 0.10 | 0.35 ± 0.10 | 0.25 ± 0.06 |
| DCE-GS (0.06 mM) | 7 | 0.16 ± 0.02 | 0.23 ± 0.05 | 0.11 ± 0.05 | 0.18 ± 0.03 |
| DCE-GS (0.6 mM) | 8 | 0.13 ± 0.01 | 0.19 ± 0.02* | 0.15 ± 0.02 | 0.13 ± 0.02 |
| DCE-GS (6 mM) | 5 | 0.13 ± 0.02 | 0.16 ± 0.02* | 0.22 ± 0.04 | 0.15 ± 0.02 |
| GSSG (0.3 mM) | 5 | 0.22 ± 0.03 | 0.17 ± 0.01* | 0.15 ± 0.03 | 0.15 ± 0.03 |

Each value is the mean ± S.E. The unit is %.
Significant difference from control group: *: $p < 0.05$.

As apparent from Table 1, the present compound inhibits the breakdown of the blood-aqueous barrier of the eye and, therefore, has a protective action on intraocular tissues. The intensity of this action of the present compound is equivalent to that of oxidized glutathione (GSSG) which is used in commercial intraocular irrigating solutions.

Example 2

Effect of the Intraocular Irrigating Solution of this Invention on Blood-Aqueous Barrier the Eye Experimental animals White rabbits weighing about 2.5 to 3.0 kg were used.

Test solution

The intraocular irrigating solution according to Formulation Example 1, which appears hereinafter, was used to evaluate its effect on the blood-aqueous barrier of the eye.

Method

Two 23 G needles connected to a polyethylene tube were gently inserted into the anterior chamber of the eye of rabbits under anesthesia (ketamine hydrochloride: xylazine hydrochloride=1:1). Using a syringe pump, the intraocular irrigating solution was infused at the rate of 1.5 ml/min., and 0.5 ml/kg off 1% carboxy-fluorescein was injected into the auricular vein immediately before and 10 and 20 minutes after irrigation. The anterior chamber irrigating solution was collected over 10 minutes after each carboxyfluorescein injection and the intensity off florescence of each sample was determined with a spectrophotofluorometer. After collection of the anterior chamber irrigating solution, 25 µl of blood was collected and mixed with 2.5 ml of physiological saline and the mixture was centrifuged at 3000 rpm to separate the supernatant for use as a sample.

The degree (%) of protein leakage was calculated by means of the following equation. (Intensity of fluorescence of irrigating solution/intensity of fluorescence of blood)× 100 (%)

Results

The results are shown in Table 2.

[TABLE 2]

Effect of the intraocular irrigating solution of this invention on the blood-aqueous barrier of the eye

| Group | Time (min.) | | |
|---|---|---|---|
| | 10 | 20 | 30 |
| Physiological saline | 0.12 ± 0.01 | 0.42 ± 0.13 | 0.27 ± 0.08 |
| Irrigating solution of Formulation Example 1 | 0.14 ± 0.03 | 0.10 ± 0.01 | 0.10 ± 0.01 |

Each value is the mean ± S.E. The unit is %.
n = 5–7.

It is apparent from Table 2 that the intraocular irrigating solution of this invention inhibits the breakdown of the blood-aqueous barrier and, therefore, has a protective action on intraocular tissues.

Reference Example 1

Acute Intravenous Toxicity Study

Using male ddY mice weighing about 20 g in groups of 5, an acute toxicity study of DCE-GS by intravenous injection was carried out. The dose levels were 100, 200 and 400 mg/kg (common ratio 2). The injections were adjusted to pH 7 with 1N-sodium hydroxide. During the observation period of 72 hours, no death occurred, nor was observed any abnormal behavior.

Formulation Example 1

| | |
|---|---|
| S-(α,β-Dicarboxyethyl)glutathione sodium | 0.09515 g |
| Glucose | 0.150 g |
| Sodium chloride | 0.710 g |
| Potassium chloride | 0.036 g |
| Calcium chloride | 0.018 g |
| Magnesium sulfate | 0.030 g |
| Sodium hydrogen carbonate | 0.210 g |
| Hydrochloric acid | q.s. |
| Sterile purified water to make | 100 ml |
| | pH 7.2 |

The above ingredients are dissolved in sterile purified water and the solution is adjusted to pH 7.2 with hydrochloric acid and filtered through a 0.22 µm filter. The Filtered solution is filled into 100 ml vials, sterilized at 100° C. for 30 minutes and air-cooled.

This intraocular irrigating solution was stable with a residue rate of the present compound of 98% after 10 months' storage at 25° C. and showed no precipitation of, in particular, calcium.

Formulation Example 2

| | |
|---|---|
| S-(α,β-Dicarboxyethyl)glutathione | 0.1 g |
| Glucose | 0.15 g |
| Sodium chloride | 0.8 g |
| Potassium chloride | 0.04 g |
| Magnesium sulfate | 0.06 g |
| 1N-sodium hydroxide | q.s. |
| Sterile purified water to make | 100 ml |
| | pH 7.3 |

The above ingredients are dissolved in sterile purified water and the solution is adjusted to pH 7.3 with 1N-sodium hydroxide and filtered through a 0.22 µm m filter. The filtered solution is filled into 100 ml vials, sterilized at 100° C. for 30 minutes and air-cooled.

The present compound contained in the intraocular irrigating solution of this invention is not only effective in protecting the intraocular tissues on the occasion of ophthalmic surgery but effectively inhibits precipitation of the calcium contained. Therefore, the intraocular irrigating solution of this invention is very stable and can be used with advantage in various kinds of ophthalmic surgery such as cataract surgery and transplantation of the cornea, iris and vitreous body.

What is claimed is:

1. A method of inhibiting precipitation of calcium in an intraocular irrigating solution which contains calcium ions by incorporating therein a compound of the formula $$\text{HOOC}-\underset{\underset{\text{NH}_2}{|}}{\text{CH}}-\text{CH}_2\text{CH}_2-\text{CONH}-\underset{\underset{\underset{\underset{\text{CH}_2-\text{COOH}}{|}}{\text{CH}_2-\text{S}-\text{CH}-\text{COOH}}}{|}}{\text{CH}}-\text{CONH}-\text{CH}_2-\text{COOH}$$

or a pharmacologically acceptable salt thereof.

2. A method of protecting intraocular tissues during ophthalmic surgery by irrigating the tissues with an intraocular irrigating solution containing an effective amount of a compound of the formula $$\text{HOOC}-\underset{\underset{\text{NH}_2}{|}}{\text{CH}}-\text{CH}_2\text{CH}_2-\text{CONH}-\underset{\underset{\underset{\underset{\text{CH}_2-\text{COOH}}{|}}{\text{CH}_2-\text{S}-\text{CH}-\text{COOH}}}{|}}{\text{CH}}-\text{CONH}-\text{CH}_2-\text{COOH}$$

or a pharmacologically acceptable salt thereof.

3. The method according to claim 2, wherein the intraocular irrigating solution further contains calcium ions.

4. The method according to claim 1, wherein the intraocular irrigating solution contains calcium ions in a concentration range of about 0.5 mM to about 5 mM.

5. A method according to claim 1 wherein the concentration of the compound or salt thereof is present in a concentration of about 0.1 mg/ml to about 10 mg/ml.

6. A method according to claim 1 wherein the intraocular irrigating solution has a pH in the range of about 6.5 to about 7.5.

7. A method according to claim 1 wherein the intraocular irrigating solution has an osmotic pressure in the range of about 260 mOsm to about 310 mOsm.

8. The method according to claim 2, wherein the intraocular irrigating solution further contains calcium ions in a concentration range of about 0.5 mM to about 5 mM.

9. A method according to claim 2 wherein the concentration of the compound or salt thereof is present in a concentration of about 0.1 mg/ml to about 10 mg/ml.

10. A method according to claim 2 wherein the intraocular irrigating solution has a pH in the range of about 6.5 to about 7.5.

11. A method according to claim 2 wherein the intraocular irrigating solution has an osmotic pressure in the range of about 260 mOsm to about 310 mOsm.

* * * * *